(12) United States Patent
Trung et al.

(10) Patent No.: US 7,604,712 B2
(45) Date of Patent: Oct. 20, 2009

(54) METHOD FOR DETERMINING CHEMICAL PULP KAPPA NUMBER WITH VISIBLE-NEAR INFRARED SPECTROMETRY

(75) Inventors: Thanh P. Trung, Vancouver (CA);
Stephen P. A. Betts, Vancouver (CA);
Denys F. Leclerc, Vancouver (CA)

(73) Assignee: FPinnovations, Pointe-Claire, Quebec (CA)

(*) Notice: Subject to any disclaimer, the term of this patent is extended or adjusted under 35 U.S.C. 154(b) by 351 days.

(21) Appl. No.: 11/364,275

(22) Filed: Mar. 1, 2006

(65) Prior Publication Data
US 2006/0196622 A1   Sep. 7, 2006

Related U.S. Application Data

(60) Provisional application No. 60/658,183, filed on Mar. 4, 2005.

(51) Int. Cl.
*D21C 7/14* (2006.01)

(52) U.S. Cl. .................... 162/49; 162/198; 162/263

(58) Field of Classification Search .......... 162/49, 162/238, 50, 196, 263
See application file for complete search history.

(56) References Cited

U.S. PATENT DOCUMENTS

| | | | |
|---|---|---|---|
| 4,743,339 A | 5/1988 | Faix et al. | |
| 5,536,942 A | 7/1996 | Barringer et al. | |
| 5,680,321 A * | 10/1997 | Helmer et al. | 702/30 |
| 5,953,111 A | 9/1999 | Millar et al. | |
| 6,475,339 B1 | 11/2002 | Chai et al. | |
| 6,551,451 B2 | 4/2003 | Trung et al. | |
| 2001/0017195 A1 | 8/2001 | Trung et al. | |
| 2003/0048440 A1 | 3/2003 | Lindgren et al. | |
| 2003/0155092 A1 | 8/2003 | Badenlid et al. | |
| 2005/0088653 A1 | 4/2005 | Coates et al. | |

FOREIGN PATENT DOCUMENTS

WO   WO 01/79816   10/2001

OTHER PUBLICATIONS kajaaniCORMECi In-line Pulp Color Sensor [downloaded online www.mediaviisi.fi],Metso Paper,Mar. 23, 2003 [downloaded on Apr. 11, 2008], whole document.*

Anttie et al., Detection of kappa number distributions in kraft pulps using NIR spectroscopy and multivariate calibration, Mar. 2000, TAPPI Press, whole document.*

(Continued)

*Primary Examiner*—Eric Hug
*Assistant Examiner*—Anthony J Calandra
(74) *Attorney, Agent, or Firm*—Ogilvy Renault LLP

(57) ABSTRACT

A method for the determination of a cellulosic-fibre property, namely, residual lignin content or Kappa number of chemical pulp, with the aid of a spectroscopic technique obtained over a range covering the visible and the near-infrared regions of the electromagnetic spectrum, comprising exposing the wet fibres to a light source covering a range in the visible region of 350 nm to 750 nm and a range in the near-infrared of 1100 nm to 2400 nm, reflecting light from the wet fibres, establishing a spectrum, comparing the spectrum with a known spectrum of the property and evaluating the comparison; the method has particular utility in a pulp manufacture line; an apparatus is described for carrying out the method.

15 Claims, 7 Drawing Sheets

OTHER PUBLICATIONS

Woitkovich et al., Annual Research Review—Mechanical Pulping, 1992, IPST, p. 69-79.*

Strube, Raman Difference Spectroscopy Under Computer Control, 1990, Journal of Raman Spectroscopy, whole document.*

High-output Infrared LED, Radio Shack [downloaded online www.radioshack.com], downloaded on Dec. 18, 2008, whole document.*

ED Chip C1200-35, Roithner-laser [downloaded online: www.roithner-lasercom/All_Datasheets/LEDs/C1200-35.pdf], downloaded on Dec. 18, 2008, whole document.*

LeClerc et al., Handbook of Vibrational Spectroscopy: Vibrational Spectroscopy in the Pulp and paper Industry, 2002, John Wiley and Sons, vol. 4, whole chapter.*

Birkett, M.D. and Gambino, M.J.T., "Estimation of Pulp Kappa Number With Near-Infrared Spectroscopy", Tappi J., 72(9): 193-197 (1989).

Pulp and Paper Magazine of Canada, Convention Issue, 1957, The "H" Factor: A Means of Expressing Cooking Times and Temperatures as a Single Variable by K.E. Vroom, pp. 228 to 231.

Tappi, Standard G-18, revised Jul. 1997—"Kappa Number of Pulp".

PAPTAC 90th Annual Meeting—2004, "Kappa Number Testing With Better Repeatability and at Lower Cost" by Zhi-Hua Jiang et al, pp. C-111 to C115.

Pulp and Paper Sep. 1998, "Online K Number Analysis Smoothes Fiberline Operation at Northwood Kraft", pp. 87 to 92.

Tappi Journal, Nov. 1987, "The STFI OPTI-Kappa Analyzer Applications and Accuracy" by Egils Kubulnieks et al, pp. 38 to 42.

SPIE vol. 665 Optical Techniques for Industrial Inspection (1986), "An Optical Approach to the Measurement of the Lignin Content of Kraft Pulps, Part A: Using Ultraviolet Measurements" by R.G. Bentley, pp. 265 to 279.

Tappi Jul. 1967, vol. 50, No. 7, "Determination of Lignin in Pulp and Paper by Infrared Multiple Internal Reflectance" by Joseph Marton et al, pp. 363 o 368.

Tappi Journal, Nov. 1987, "Estimation of Lignin in Wood Pulp by Diffuse Reflectance Fourier-Transform Infrared Spectrometry" by Sally A. Berben et al, pp. 129 to 133.

1993 Pulping Conference, "At-Line Kappa Number Measurement by Near-Infrared Spectroscopy" by Ertan Yuzak et al, pp. 663 to 671.

Journal of Wood Chemistry and Technology, vol. 24, No. 1, 2004, "Predicting Extractives and Lignin Contents in Eucalyptus Globulus Using Near Infrared Reflectance Analysis" by Fiona S. Poke et al, pp. 55-67.

Shen et al., Study of on-line pulp Kappa number determination . . . , 58th Appita annual conference . . . , Technical Association . . . Pulp and Paper, Appita 2004, vol. 2, pp. 501-505.

Shen et al, Study of on-line measurement of pulp Kappa number . . . . TAPPI Technology Summit 2002, Technical Association of the pulp and paper industry, pp. 17-22.

Liljenberg et al., On-line NIR characterization of pulp, 10th International symposium on wood and pulping chemistry, 1999, 10 sup. pp. 266-269.

* cited by examiner

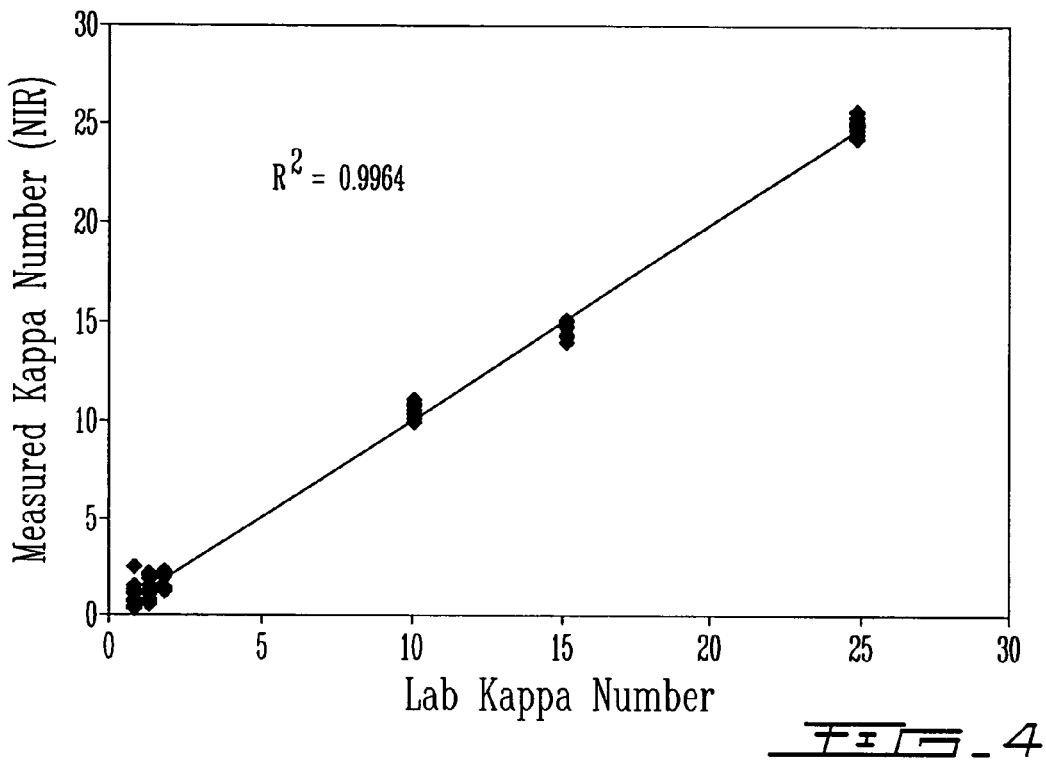
FIG_4
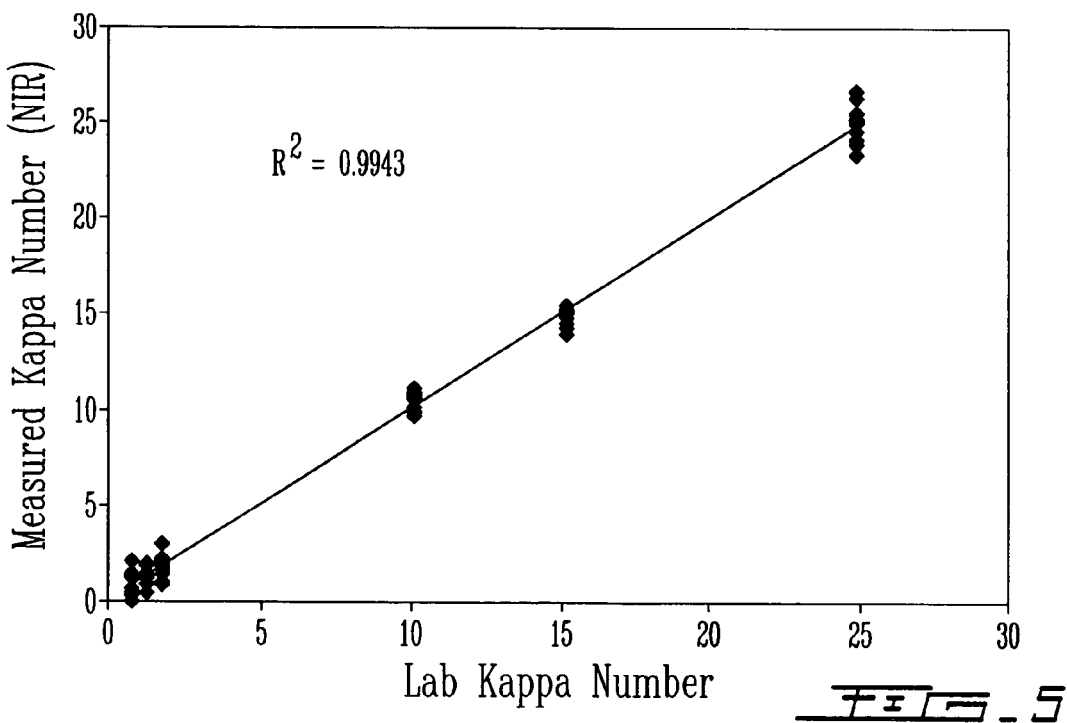
FIG_5

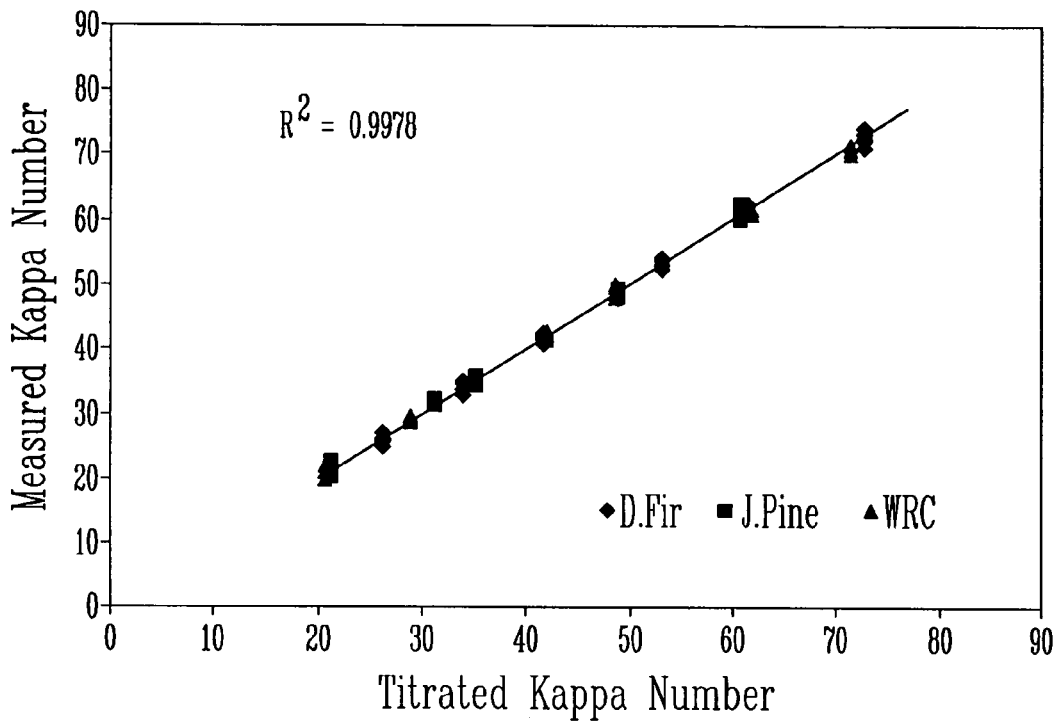
FIG_6
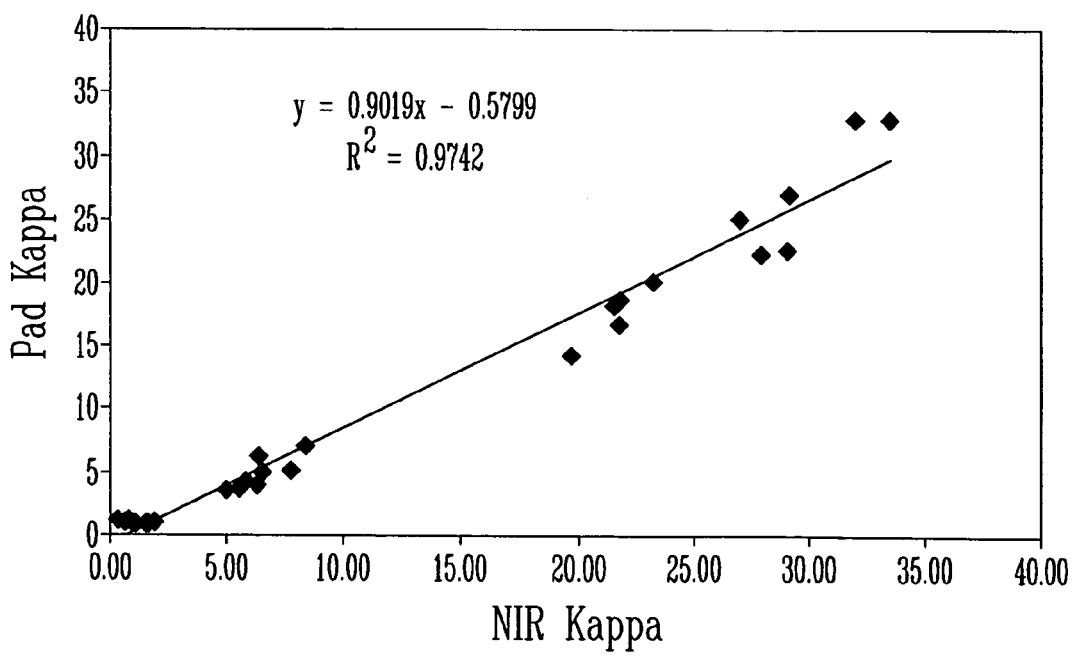
FIG_7

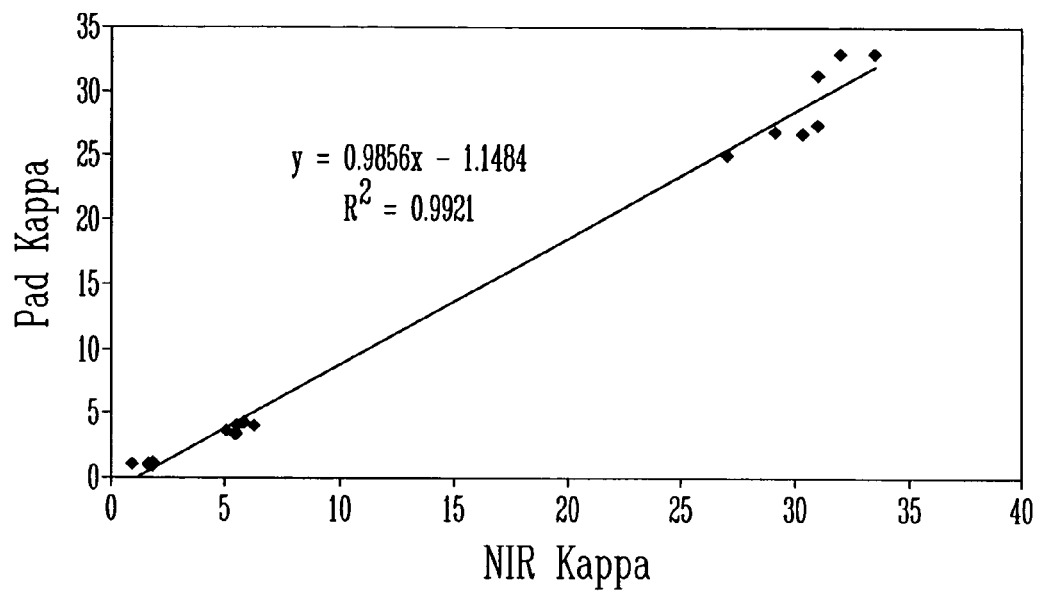
FIG_8
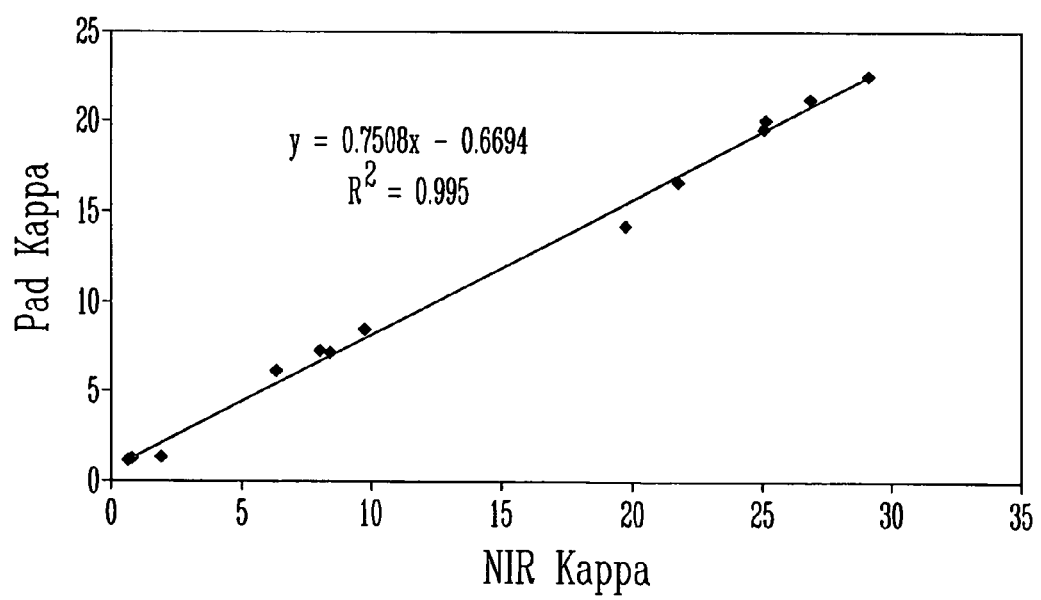
FIG_9

METHOD FOR DETERMINING CHEMICAL PULP KAPPA NUMBER WITH VISIBLE-NEAR INFRARED SPECTROMETRY

This application claims priority from U.S. Provisional Patent Application No. 60/658,183 filed Mar. 4, 2005.

BACKGROUND OF THE INVENTION (i) Field of the Invention

The instant invention relates to a novel method of measuring fibre properties, particularly residual lignin content of chemical pulp, with the aid of a fast scanning spectrometer in the combined visible and near infrared spectral regions.

(ii) Description of the Prior Art

The accurate on-line measurement of the Kappa number of chemical pulps obtained from rapidly varying furnishes remains an unresolved issue for chemical pulp manufacturers. Mills that use residual sawmill-chips from various locations and those producing specialty grades are especially affected because of the variability of chip quality from various suppliers. This issue is even more prevalent now due to a shortage of available market wood chips and the fact that pulp and paper mills are being forced to purchase chips geographically distant from their manufacturing facilities. All too often, pulp produced during grade changes, or from poorly characterized chip species mixtures, has to be downgraded because of a high proportion of improperly cooked pulp, since each wood chip species cooks differently. Analysers capable of rapid determination of Kappa number could help mills greatly reduce Kappa number variation, bleaching costs and the amount of off-grade pulp.

Current digester control algorithms use the blow-line Kappa number in conjunction with the H-factor [1] for controlling the pulping operation. Generally, Kappa number measurements are required as a feedback parameter to allow for adjustments in the liquor charged to the digester at the various zones of the cook and, much more critically, as a feed-forward parameter for control of the bleach plant. Higher Kappa number pulp requires higher charges of bleaching chemical to reach target final pulp brightness levels, particularly during the oxygen-delignification stage.

The measurement of residual lignin content in pulp has been traditionally done on an hourly basis as a laboratory analysis according to TAPPI standard method T236 [2] which uses a back titration of residual permanganate with potassium iodide. However, the method requires extensive workup and can take 30 to 60 minutes per sample. Jiang et al. [3] have improved on this standard technique by semi-automating the titration process with an automatic, multi-sample titrator. More recently, Chai et al. [4] have proposed the use of rapid acidification to improve the accuracy of the potassium permanganate titration. Manganese dioxide precipitation is prevented and thus residual permanganate can be analysed without spectral interference from $MnO_2$ and allowing the UV-visible spectrometry technique to be more accurate than by titration. However, this method still requires sample preparation, a number of reagents and a chemical reaction which takes between three to five minutes to complete. The time delay limits the utility of this method for feedback control of the digester and for feed-forward control of the bleach plant.

Current commercially available Kappa number analysers use UV light with a combination of reflectance, scattering, transmittance, and consistency measurements [5-6] to analyse pulp samples with frequencies in the order of 10 to 20 minutes. These methods (STFI, Metso, and BTG) utilize a transparent cell/chamber through which a thoroughly washed pulp, diluted to a known consistency (0.1% to 0.4%) is circulated, whereby the reflected and transmitted light is collected at some predetermined UV or visible wavelengths over a period of one or more minutes, and a consistency-corrected Kappa number is determined from these readings so as to account for the change in reflected intensity which is strongly dependent on consistency. The UV-sensor is used to measure residual lignin while the visible light is used for consistency measurement. A typical routine requires extensive washing to remove excessive residual liquor. Dilution is then carried out to approximate volume and the pulp slurry is circulated and a separate detector is used for consistency determination. If the consistency is not within the desired range, the dilution is adjusted and the pulp mixture is then again re-measured. Upon reaching the desired consistency, Kappa measurements are made. Although the principle is simple, the actual measurement is complex because lignin absorption cannot be measured accurately without accounting for the interferences produced by changes in pulp consistency and furnish. This problem can be addressed by building two-point calibrations that are valid for a relatively narrow range of sampling conditions. Calibrations are prepared by characterising the relationship between the three types of measurement at a given optimal consistency, and are reported to be satisfactory for bleach-plant samples [6], single-species furnishes and stable, well characterised mixed furnishes of constant composition.

Currently available commercial kappa analysers do not provide accurate results for furnishes of unknown or rapidly changing composition [7]. When the composition of chips is constantly changing, instruments have to be constantly re-calibrated to follow the changes in furnish. Updating the two-point calibration and the sampling system requires constant attention from instrumentation personnel. Furthermore, owing to the added sample preparation step, throughput is relatively low, allowing throughput of only about two samples per hour for each location.

Lignin chemists have been using vibrational spectroscopy for nearly fifty years to characterise wood and pulp samples. Marton and Sparks [8] have determined the Kappa number of pulps by using the area beneath the lignin peak at 1510 cm$^{-1}$ and the cellulose peak at 1100 cm$^{-1}$ as an internal standard. The lignin/cellulose peak-area ratio was found to be insensitive to variations in basis weight. Similarly, Berben et al. [9] developed a method using infrared diffuse reflectance for estimating lignin content in unbleached pulp. A linear relationship for all species combined is found between the area of the band at 1510 cm$^{-1}$ and Kappa number for a wide variety of species. However, these methods used dry pulp samples and are not amenable to online process analysis of Kappa number for process control.

U.S. Pat. No. 4,743,339 [10] illustrates a method for determining pulp properties, including Kappa number using FT-IR in the spectral range of 6300 nm to 7800 nm. In this method, a spectrum, acquired with 200 co-add averages, needs to be baseline corrected by first determining the water content and fibre content (consistency). This method is extremely sensitive to consistency since it must be determined so as to provide an accurate baseline correction. Another short-coming of this method is that it is sensitive to species and must be recalibrated with changes in digester furnish. Furthermore, the number of scans limits this measurement technique as an online analyser since it takes over 15 minutes for each spectral acquisition, not including the sample preparation time, and must be performed at room temperature.

Yuzak and Lohrke [11] detailed the results of a series of experiments and showed that NIR can be used to estimate the Kappa number of properly prepared kraft pulp samples, i.e. dried handsheets, with an error of ±2.0 Kappa. The authors concluded that, through their series of sample pre-treatment methods, NIR spectral model for the determination of Kappa number are: 1. Without pre-treatment—unacceptable, 2. Hose-washed—unacceptable (error −9.0 to +11.7), 3. Hose-washed and filtered—unacceptable (error −11.8 to +4.3), 4. Hosed-washed+blended+filtered+pressed—unacceptable (error −0.3 to −15.2), 5. Hose-washed+blended+dried (handsheet)—acceptable (error ±2.0 Kappa). Even though the authors utilized the spectral region of 1500-1750 nm and 2100-2400 nm, their reliance on homogenizing and drying the samples effectively teaches away from using NIR spectrometry as a rapid on-line method for determining Kappa numbers.

U.S. Pat. No. 5,536,942 [12] describes a method and apparatus for the measurement of properties, including Kappa number, of fibres in a fibre suspension with the aid of an NIR spectrometer. The invention details the steps and apparatus for extracting the samples from the process stream, repeated washing in a chamber, and pumping the diluted solution to a cell which incorporates a screen whereby the fibres are concentrated and monitored at 950 nm to an absorbance of 2.0 to 4.5 absorbance unit (A.U.) to obtain the preferred consistency (3%), and registering with the detector to obtain a transmission NIR spectrum in the range of 850 nm to 1050 nm. The sample is then re-homogenized by backflushing the cell and re-concentrating the fibres on the screens then repeating the acquisition. This method also heavily relies on the measurement of consistency and operates at high absorbance range, outside the typical linear Beer-Lambert's law and reaching the limit of linear range of many instruments. As a result, for the range of consistencies used by U.S. Pat. No. 5,536,942, slight errors in the absorbance would translate into large errors associated with Kappa-number determination. In addition, the requirement of extensive washing and concentrating prior to spectral data acquisition then followed by re-homogenizing and concentrating and data acquisition also limits the true online feasibility of the measurement technique for process control.

PCT Patent WO 01/79816 [13] describes a method for the determination of physical properties of fibre suspensions such as viscosity, tensile strength, fibre lengths, density, burst index, coarseness, opacity, beating requirement, light scattering, zero span as well as chemical compositions such as lignin and hexanuronic acid. The sample is withdrawn from the process and is washed to provide clean pulp which is diluted to two streams with one partial flow to be dewatered and dried and used for spectroscopic analysis while the second partial flow is used for analysis of physical fibre data by means of image analysis. The two data sets are combined with multivariate data processing for predictions of physical fibre properties. The method states that the correlation is improved with the combination of data from the FibreMaster and NIR data. Spectroscopic measurement is made in the NIR range from 780 nm to 2500 nm. The diluted sample needs to be dried to a solids content of at least 50%, preferably 70%, which is accomplished by filtering and forced air drying preferably by means of direct contact with compressed air. The method further states that the drying process takes time, but the image analysis also takes time and this allows for the synchronization between the two techniques. As such, the throughput of the stated method can only reach four analyses per hour, and as described is unsuitable for an on-line application. Also, no data for Kappa number was presented.

Birkett and Gambino [14] further details the result as obtained with a filtometer or filter-based spectrometer and showed correlations for handsheets kappa number made from *Eucalyptus* grandis and 5 specific wavelengths that have been optimized by multilinear regression. The author showed that there is species dependency associated with filter-based spectrometers as models developed for E. grandis were not able to provide acceptable results as determined by the overall calibration model (p. 195, $1^{st}$ par., line 5 to 17). The author further states that, (p. 195, par. 3, lines 1-3) " . . . that calibrations for pine and eucalyptus should be treated separately" and that " . . . it may be necessary to calibrate for a specific species . . . ". Furthermore, the author is providing results done with dried handsheets of pulp. Birkett and Gambino acknowledges this particular matter by stating that the results are obtained with dried handsheets and that " . . . the ability to use NIRS on wet pulp obviously would make process control easier and faster" (p. 196, par. 1, lines 8-13). Birkett and Gambino showed that filtered-based NIR system is sensitive to species variation and can only be applied to dried handsheets.

U.S. Pat. No. 5,953,11 [15], Millar et. al. describes the use of a continuous in-line kappa measurement system whereby light from an excitation source is injected into a flowing conduit carrying pulp. Reflected light is collected with two detectors, one at near-proximity and one at far-proximity along with a light-source feed back as a reference. The reflected light collected at the near-proximity and far-proximity detectors are normalized with the reference and used for calculations of kappa number. The illumination light is made up of individual specific wavelengths in the visible spectral consisting of a wavelength in the blue region, green region, amber, and red region (page 6, paragraph 4, line 7-10). As with many other systems currently available, this system mainly relies on the lignin absorbance in the visible region of single wavelength, as in a filtometer or filter-based visible spectrometer. Though filter-based systems are relatively inexpensive and can be configured with many different wavelengths, filter-based system suffer from wavelength accuracy from filter-to-filter due to manufacturing processes as well as calibration drifts and the extensive calibration requirements due to system to system differences. Furthermore, Birkett and Gambino [14], above, showed that NIR filter-based system can not handle species variation and requires dried handsheets in order to provide acceptable kappa number for process control. Due to these shortcomings and difficulties, filter-based systems are generally not successful as online analysers.

Poke et al., [16] present a NIR method for the determination of lignin in wood meal, which requires the drying and grinding of samples. Again, this method is clearly unsuitable for an-on-line application.

To overcome the limitations of NIR spectrometry, Trung et al. [17] have proposed the use of visible-excitation Raman spectroscopy for measuring lignin in pulp. Even though this method overcomes some of the limitations associated with laser-induced fluorescence, this method requires the preparation of a high-consistency sample (15 to 30%) and a relatively long acquisition time (5 to 10 minutes), primarily because of the inherent weakness of the Raman signal produced by the small illumination spot used in the application. The small illumination spot limits the amount of pulp being sampled through poor sub-sampling, thereby increasing the likelihood of getting a non-representative sample for analysis. This will increase the uncertainty of the measurement since Kappa number is known to vary significantly from fibre-to-fibre, within a cook.

Therefore, the prior art clearly teaches away from the use of NIR spectrometry for determining Kappa number on wet pulp samples, especially if one wishes to perform any rapid, on-line quantitative analysis. Unexpectedly, the instant invention provides a very rapid method for the quantitative determination of lignin content or Kappa number in wet pulp samples. As NIR spectrometry is repeatedly described in the prior art as being quite sensitive to moisture content, this further teaches those skilled in the art of pulp analysis, away from applying NIR spectrometry for the measurement of lignin content or Kappa number. None of the methods cited in the prior art is capable of determining lignin content with sufficient accuracy and detail to yield a useful measurement for process and/or quality control. In the following, we disclose such a method. The instant invention overcomes the limitations described above by performing measurements on a large amount of pulp, and, unlike the prior art, can also tolerate moderate variations in consistency.

SUMMARY OF THE INVENTION

The object of the instant invention is to provide a method for determining the properties of chemical pulp fibres, particularly, but not limited to, the residual lignin content of chemical pulps, in which the shortcomings of the prior art are overcome and to provide true online process monitoring on the order of seconds without sample preparation such as drying and consistency measurement.

In accordance with one embodiment of the invention, there is provided a method for determining a pulp property of chemical pulp fibres comprising: a) exposing pulp fibres derived from at least partially digested wood chips to light covering a range in the visible region of 350 nm to 750 mm and a range in the near-infrared (NIR) region of 1100 to 2400 nm, and allowing the pulp fibres to reflect the light, b) collecting light reflected from said fibres, c) establishing a spectrum of the reflected light, d) comparing said spectrum with a spectrum of chemical pulp fibres for which the pulp property is known, and e) evaluating the pulp property from the comparison in d).

In accordance with another embodiment of the invention, there is provided in a pulp fibre manufacture line having a digester for cooking wood chips, and pulp washing and bleaching stations, and having means for determining a pulp property of pulp fibres in the line, the improvement wherein said means comprises: i) a light source adapted to expose said pulp fibres, at at-least one location in said line to light covering a range in the visible region of 350 nm to 750 mm and a range in the near-infrared (NIR) region of 1100 to 2400 nm, ii) a spectrometer to collect light reflected from pulp fibres exposed to said light source and establish a spectrum of the reflected light, and iii) comparison means for comparing the spectrum established in ii) with a spectrum of pulp fibres of known pulp property and from which the property of the pulp fibres in i) can be determined.

In a particularly preferred embodiment, the means for determining the pulp property is in the line downstream of the digester.

In a specific embodiment, the invention relates to a novel method for the determination of cellulosic-fibre properties, such as that, but not limited to, residual lignin content of chemical pulp with the aid of a spectroscopic technique obtained over a range in the electromagnetic radiation region covering the visible (350 to 750 nm) and the near-infrared (NIR) (1100 to 2400 nm), comprising the steps of obtaining the fibres from the process, removing excess water, illuminating the fibres, or fibre clusters with a large beam excitation source, optionally moving the sample at a constant speed, collecting the diffused reflected light with a fibre-optic probe, registering said reflected light with one or more detectors, for example three detectors, for a predetermined time, and logging the spectrum and correlating the spectral data with the aid of a computer and a previously prepared calibration model, and determining the pulp properties of said sample.

BRIEF DESCRIPTION OF THE DRAWINGS

FIG. 4 is a graph showing the correlation between laboratory titrated Kappa number versus NIR determined Kappa number using the teaching of one prior art;

FIG. 5 is a graph showing the correlation between laboratory titrated Kappa number versus NIR determined Kappa number using the teaching of one prior art (850-1050 nm);

FIG. 6 is a graph showing the correlation between the NIR Kappa number determined by instant invention for three different wood species. A similar, but separate calibration is obtained for hardwoods;

FIG. 7 is a graph showing the correlation between Kappa number derived in accordance with the invention (NIR Kappa) and laboratory titration results for Kappa;

FIG. 8 is a graph similar to FIG. 7 for three different furnishes or grades; specifically grade A, produced from A-mill, and comprises hemlock, cedar, and mixtures of SPF in proportions of 60%, 20%, and 20%, respectively;

FIG. 9 is a graph similar to FIG. 8 but for grade B, produced from B-mill, and comprises of hemlock and mixtures of SPF with proportions of 80% and 20%, respectively;

DETAILED DESCRIPTION OF THE PREFERRED EMBODIMENTS OF THE INVENTION

Figure 1:
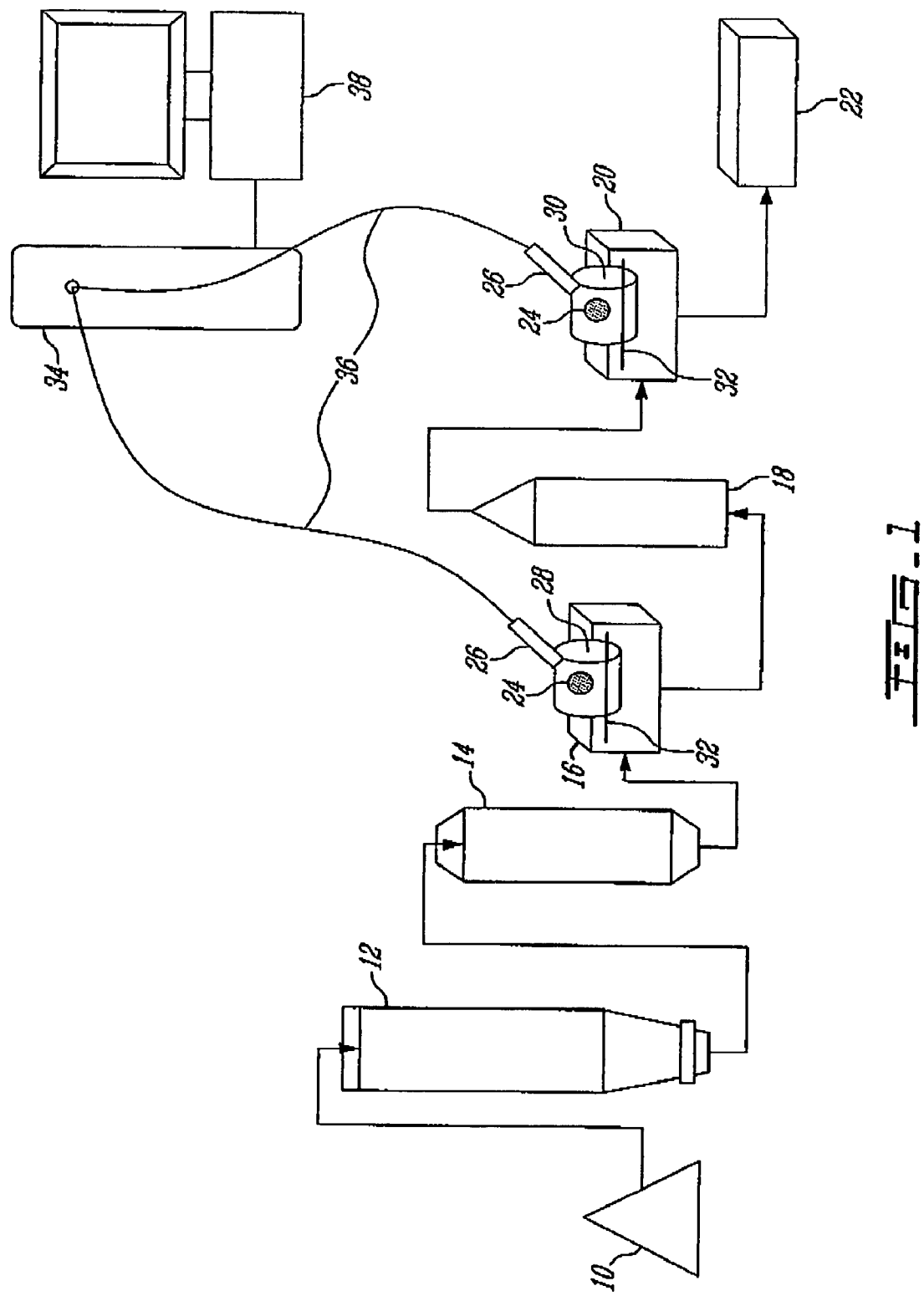
FIG. 1 is a schematic view of referred installation configuration in accordance with the invention in which an excitation source and a probe are located at the brownstock washer drum and bleach plant washer drums.

Referring to FIG. 1, wood chips 10 are introduced into a digester 12 and mixed with cooking chemicals to release the lignin from the woody matrix to yield pulp fibres. Pulp fibres are then blown into a blow tank 14 to which water is added and the stock is pumped to brownstock washers 16. The stock is washed through multiple washers 16 and then bleached in multiple towers 18 and washers 20 before being sent to a paper machine 22.

An arrangement, and preferably, as well as other variants thereof, for online measurement with the instant invention includes the mounting of an excitation light source 24 and a fibre-optic probe 26 along the various locations of the kraft pulping process and bleaching process, such as at the brownstock washer drum 28, and bleach plant washer drum 30, just before the doctor blade 32, connected to a fast scanning spectrometer 34, via fibre optic cables 36, with a computer 38 sequencing spectral acquisitions and correlating the resulting spectrum against a predetermined calibration, and logging the results.

Figure 2:
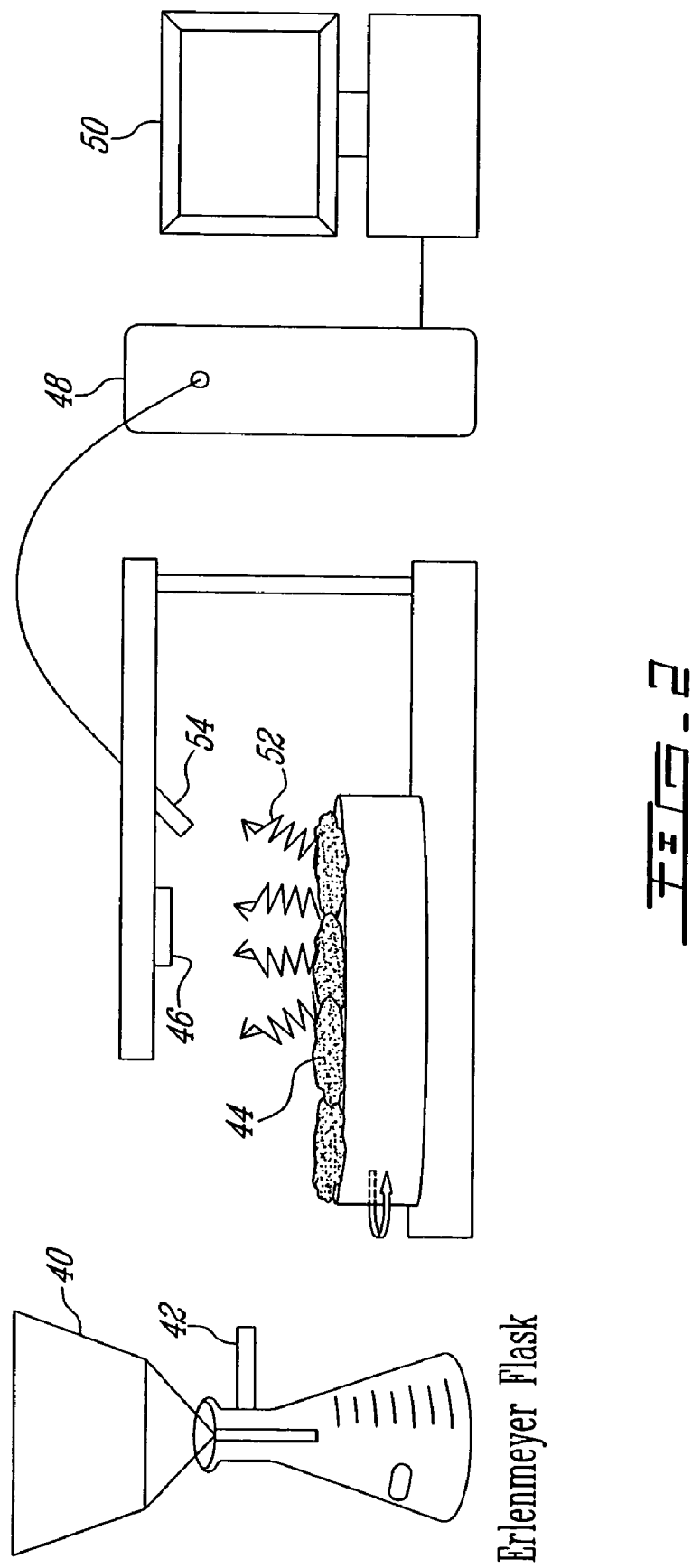
FIG. 2 is a schematic view of an alternate installation and use of the instant invention for laboratory offline analysis of pulp fibre properties, including Kappa number.

For laboratory analysis, the present invention allows for rapid analysis of pulp Kappa number with minimal sample preparation. Referring to FIG. 2, pulp samples are collected from the desired process lines, brought to the lab and washed to remove black liquor (if required) by filtering through a Buchner funnel 40, allowing most of the excess water to be removed with vacuum flask 42, and presenting pulp fibres 44 to an excitation source 46 for spectral data collection. A high speed scanning spectrometer 48, controlled by a personal computer 50, registers diffusedly reflected light 52 through fibre-optic probe 54, records a spectrum, and calculates the residual lignin concentration from said spectrum. Spectral data is collected in the range of 350 nm to 2500 nm. Within this range, more preferable spectral regions of 350 nm to 750 nm and 1100 nm to 2400 nm are used for calibration.

Within the spectral region of 350 nm to 750 nm, the region of 400 nm to 750 nm is more preferred. In general, the region below 400 nm, i.e. between 350 nm and 400 nm displays spectra which are noisy and thus is less valuable in the information that it provides.

The spectrum produced is a continuous spectrum from 350 nm to 2500 nm, preferably 400 nm to 2400 nm, however, the region of between 750 nm and 1100 nm may be blocked out, if desired, and better results are obtained when this latter region is blocked out.

The spectrum is established based on the chemical composition of the pulp, for example, the residual lignin content. The excitation light interacts with the pulp exposed to the light and at various specific frequencies, absorption, for example lignin absorption, occurs and the changes in intensity associated with such lignin absorptions are recorded as a measure of residual lignin content of the pulp.

While the method is particularly described for determining lignin content, it can similarly be employed for determining other pulp properties, for example Kappa number or ISO brightness.

Calibration for use in the instant invention is developed with the aid of multivariate analysis techniques such as partial least squares, principal component analysis and variants of such. The model developed contains any variations that can be anticipated in the process streams, including extreme swings in the fibre properties, to allow for robustness. Variations to be included in the MVA calibration include consistency (5% to 30%), wood species and Kappa numbers (0.5 to 110 Kappa). More details of MVA can be found elsewhere.

At each of the washers, a vacuum is provided to remove excessive water. The spectral data is acquired while the drums are in motion to provide good representation of the pulp samples. In this more preferred configuration, the instant invention removes the requirement of sampling devices and provides instant and continuous Kappa results for process control.

In preferred embodiments, the pulp fibres have a consistency of 8 to 30%; if necessary, excess water may be removed from the pulp fibres prior to exposing them to the light, for the determination of the desired pulp property.

The pulp fibres may suitably be mobile during the determination steps, and conveniently may be housed in a chamber which is rotated at a constant rate of revolution, during the steps of exposing the pulp fibres to the light, and collecting the reflected light. The collecting of reflected light may be carried out in a predetermined period of time which is short compared to time periods required in prior procedures, more especially less than 60 seconds, and still more especially less than 10 seconds. On the other hand, the sample can be stationary or moving and no difference in results have been observed when measuring the sample when stationary and when moving at up to 10 ft/sec. Sample movement and data collection results in an averaging effect, and as the sample moves faster more averaging is observed so that results for the bulk material remain accurate.

The method of the invention can be applied to the determination of the pulp property at different stages of the pulp manufacture, whereby, for example, continuous measurement of Kappa number is provided for feedforward and feedback control of the working and bleaching process in pulp production, to provide a pulp product of desired Kappa number.

The instant invention, which utilizes a combination of more preferred spectral regions (350 nm to 750 nm and 1100 nm to 2400 nm), features a large illuminated spot and sub-sampling to provide clear advantages over prior art. From the individual and combined teaching of the prior art, which teaches away from analyzing wet samples and to use non-optimized spectral regions, and which is further complicated by the requirement for extracting, washing, concentrating, and homogenizing, the present invention has overcome all of these limitations of previous teachings and can instantaneously provide continuous residual lignin determination.

The method can also be applied to pulp fibres before digestion is completed, i.e. during the digestion phase. In this case, the pulp fibres are of partially digested wood chips. This provides a means of monitoring the digestion. Preferably, however, the method is applied to pulp fibres after completion of the digestion, i.e. downstream of the digester in the pulp manufacture line.

The instant invention thus provides a method for determining the properties of chemical pulp fibres, particularly, but not limited to, the residual lignin content of chemical pulps, in which the shortcomings of the prior art are overcome and provides true online process monitoring in the order of seconds without sample preparation, such as drying and consistency measurement.

Experimental

Experiments were carried out with an Analytical Spectral Device (ASD, Boulder, Co.), more especially a Visible/NIR spectrometer capable of providing a complete scan from 350 nm to 2500 nm in 100 milliseconds. The unit is compact and can be operated with a battery power pack for field operations. Data was collected and averaged over 40 scans in the complete spectral range, requiring 4 seconds.

EXAMPLE 1

Figure 3:
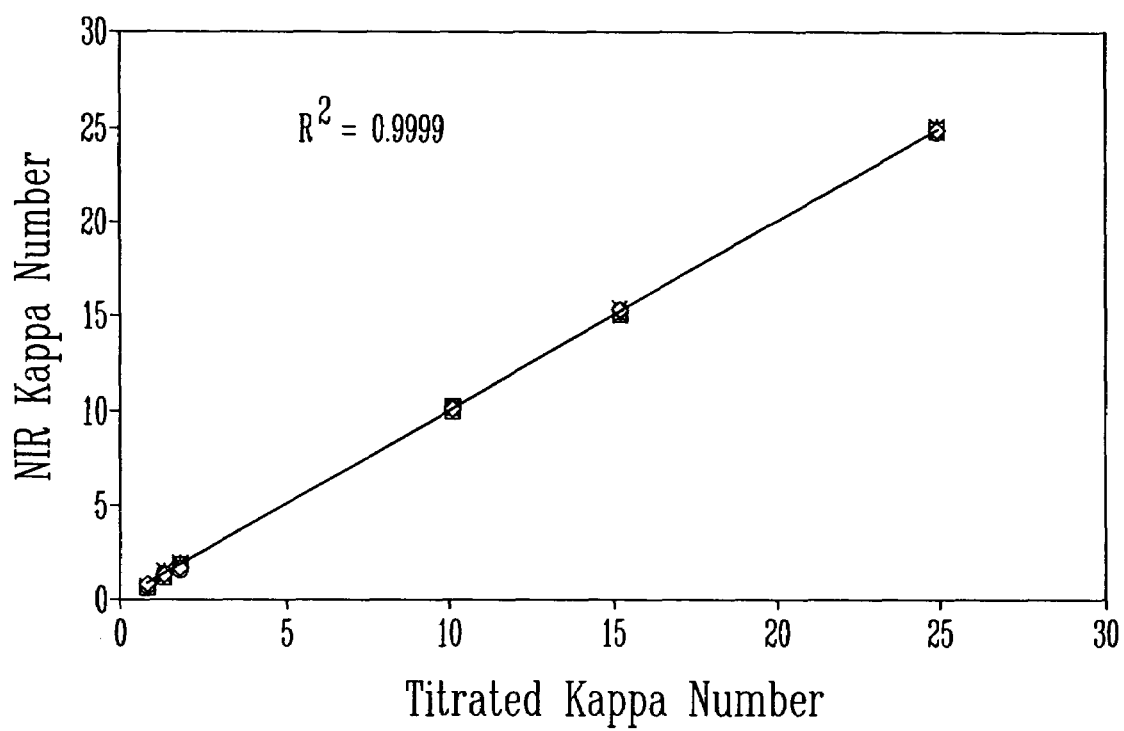
FIG. 3 is a graph showing the correlation between the Kappa number determined by standard analysis technique versus the NIR determined Kappa number of instant invention.

Pulp fibre samples were first hand-squeezed to remove excess water and placed on the sample tray. During data collection, the tray was spinning to provide better averages and improve statistical significance. FIG. 3 shows the results obtained for hemlock pulp sampled at the final brownstock washer and throughout the various washers of the bleach plant. Partial least squares multivariate calibration is used to generate the calibration using a combination of preferred spectral regions 350 nm to 750 nm and 1100 nm to 2400 nm. Six factors were used to generate the model shown yielding an $R^2$ of 0.9999. Note that there are 10 data points at each concentration level, showing the extremely good reproducibility of the instant invention. The root mean square standard error of prediction (RMSEP) is 0.2 Kappa with a reproducibility of 0.05 Kappa. Furthermore, these results also indicate instant invention is capable of measuring the residual lignin content of fully bleached chemical pulp down to market level (90+) brightness. Finally, these results were obtained with pulp fibres that have varying consistency, ranging from 8% to 30%, and which were wet. The combined teaching of the prior art above clearly indicates that good results such as shown in instant invention can only be obtained on either dry handsheets or pulp with 70% consistency.

EXAMPLE 2

FIG. 4 shows the results generated with the same dataset as above, but the calibration region is chosen to span only the NIR range of 1100 nm to 2500 nm, as indicated by the prior art. The results show inferior data, with a prediction error of ±2 Kappa which is much higher than in the results obtained in the present invention.

EXAMPLE 3

FIG. 5 shows the results obtained with the same dataset above, but calibrated in a spectral range of another prior art teaching, namely 850 nm to 1050 nm. As shown, the result obtained with the prior teaching again teaches away from the current invention since the errors in the predictions are in the order of ±4 Kappa.

EXAMPLE 4

FIG. 6 shows the results of the instant invention for residual lignin determination obtained for pulp fibres from various wood species, including, but not limited to, Douglas fir, hemlock, spruce, Jack pine, balsam fir, and western red cedar. As shown, excellent correlation is obtained and a single calibration is applicable to all softwood species, indicating that the instant invention is not affected by furnish variations. Similar results were obtained as a separate calibration for hardwood pulp fibres (not shown) with instant invention.

EXAMPLE 5

FIG. 7 illustrates the kappa number results obtained from mill installation of present invention, as obtained with mill technical staffs and operators. Excellent correlations were obtained between present invention and mill personnel, indicating utility of instant invention. Data were collected over a two week period whereby mill personnel obtained samples from the process line and perform laboratory tests for comparison between present invention and laboratory standard method. Note that present invention can provide kappa number measurements to sub 1-unit kappa number. This is unexpected as no other technique is capable of providing such low detection limit.

EXAMPLE 6

Figure 10:
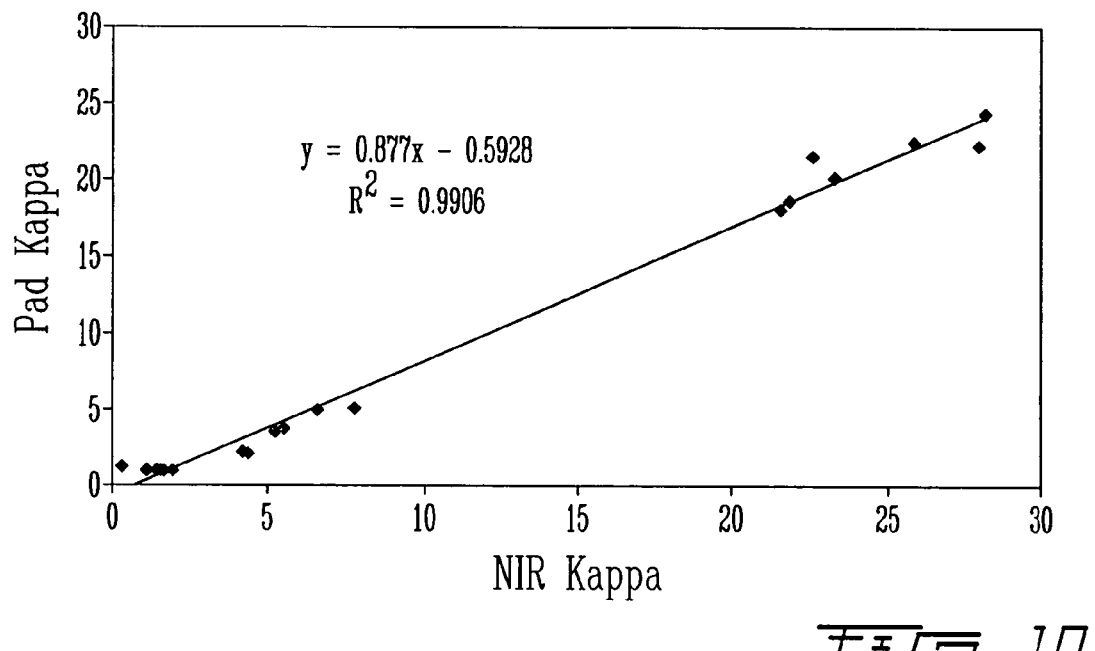
FIG. 10 is a graph similar to FIG. 8 but for grade C, produced from C-mill, and comprises Douglas fir and SPF mixtures in proportions of 80%, and 20%, respectively.

FIGS. 8-10 further illustrate the utility of present invention. The method of the invention was carried out in mill installations having varying grade changes and species mixes. Correlations between the present invention and standard laboratory analyses for A-mill, B-mill, and C-mill, which produces pulp of three different grades, grade-A, grade-B, and grade-C, are shown. Each process line pulps different species, mainly Western Red Cedar, Douglas Fir, hemlock, and other spruce-pine-fir (SPF) mixtures. The species composition for grade-A consists of 60% hemlock, 20% cedar, and 20% SPF, while grade-B consists of 80% hemlock, and 20% SPF, and grade-C consists of 80% Douglas fir and 20% SPF. Data show that instant invention can be applied to real pulp process with sufficient accuracy for process control and optimization and can span varies species mix and grade changes.

EXAMPLE 7

Figure 11:
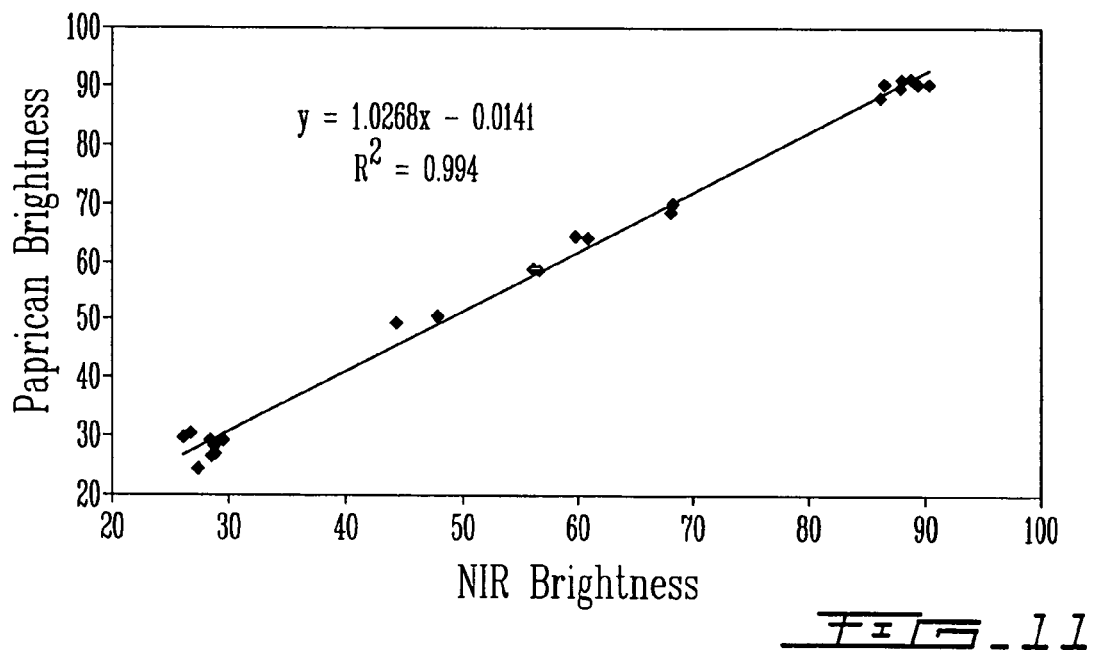
FIG. 11 is a graph showing correlation between ISO brightness of pulp as determined by the invention (NIR ISO Brightness) and laboratory determined ISO brightness of the pulp.

FIG. 11 compares the mill installation results achieved with the method of the invention with that of laboratory standard technique for ISO brightness. The method can provide ISO brightness simultaneously for further control ability of the pulp washing and bleaching processes.

FIGS. 3 to 11 are further described hereinafter:

FIG. 3 is a plot of titrated Kappa number versus NIR number. Correlation between standard analysis technique for titrated Kappa number versus the NIR determined Kappa number of instant invention. Excellent correlation is observed, right from unbleached to fully bleached pulp fibres, down to 0.5 Kappa number. Note that the different colour points are to help show that each Kappa contains 10 data points, indicating excellent reproducibility.

FIG. 4 is a plot of laboratory Kappa number versus NIR Kappa number (1100-2500 nm). Correlation between laboratory titrated Kappa number versus NIR determined Kappa number using the teaching of one prior art. Note the large spread of the data, especially for the fully bleached pulp fibres with low Kappa number.

FIG. 5 is a plot of laboratory Kappa number versus NIR Kappa number (850-1050 nm). Correlation between lab. titrated Kappa number versus NIR determined Kappa number using the teaching of one prior art (850-1050 nm). Note the large spread of the data resulting errors of ±5 or more. As a result, this technique is inferior to instant invention and would be of limited use for online process control of digester and bleach plant operations.

FIG. 6 is a plot of titrated Kappa number versus NIR Kappa number for varying wood species pulp. Correlation between NIR Kappa number determined by instant invention versus titrated Kappa. Result shows that instant invention is not dependent on wood species: shown here are correlations for, but not limited to, Douglas fir, Jack pine, and western red cedar.

FIG. 7 is a plot of mill installation results showing the correlations between instant invention and laboratory titrated results for kappa number. Results show that instant invention can provide kappa number measurements from brown stock to that of fully bleached pulp of high market brightness. It is not know of any such system that can provide kappa measurements down to kappa number of below 1-unit.

FIG. 8 is a plot of mill installation results obtained in mill with three different furnishes/grades, specifically of grade A with species composition of 40% hemlock, 20% cedar, 40% SPF, showing excellent correlation between present invention and laboratory titration with standard laboratory analyses.

FIG. 9 is a plot of mill installation results obtained in mill with three different furnishes/grades, specifically of grade B with species composition of 80% hemlock and 20% SPF, showing excellent correlation between present invention and laboratory titration with standard laboratory analyses.

FIG. 10 is a plot of mill installation results obtained in mill with three different furnishes/grades, specifically of grade C with species composition of 80% cedar and 20% SPF, showing excellent correlation between present invention and laboratory titration with standard laboratory analyses. Mill installation results validate the utility of instant invention for process manufacturing application with varying species mix.

FIG. 11 is a plot of mill installation results illustrating the use of instant invention to measure, as an option, the ISO brightness of the pulp. As such, with instant invention, though not claimed, can provide simultaneous kappa number as well as ISO brightness determination within seconds.

REFERENCES

1. VROOM, K. E., "The H Factor: A Means of Expressing Cooking Times and Temperatures as a Single Variable", *Pulp Paper Mag. Can.* 58(3): 228-231 (1957).
2. "T236—Kappa Number of Pulp", TAPPI Standard Methods, TAPPI PRESS, Atlanta; "G.18—Kappa Number of Pulp", Standard Methods of the Technical Section of the CPPA, Montreal.
3. JIANG, Z.-H., AUDET, A., van LIEROP, B. and BERRY, R. M., "Kappa Number Testing with Better Repeatability and at a Lower Cost", PAPTAC 90$^{th}$ Annual Meeting (Jan. 27-29, 2004) C-111-115.
4. CHAI, X.-S., and ZHU, J.-Y., "Method for Rapidly Determining a Pulp Kappa Number Using Spectrophotometry", U.S. Pat. No. 6,475,339 (Nov. 5, 2002).
5. YEAGER, R., "Online K Number Analysis Smoothes Fiberline Operation at Northwood Kraft", *Pulp and Paper,* 72(9): 87-88, 91-92 (1998).
6. KUBULNIEKS, E., LUNDQVIST, S.-O., PETTERSSON, T., "The STFI OPTI-Kappa Analyser—Applications and Accuracy", *Tappi J.,* 70(11): 38-42 (1987).
7. BENTLEY, R. G., "An optical Approach to the Measurement of the Lignin Content of Kraft Pulps. Part A: Ultraviolet Measurements". *Proc. SPIE,* 665: 265-279 (1986).
8. MARTON, J., SPARKS, H. E., "Determination of Lignin in Pulp and Paper by Infrared Multiple Internal Reflectance", *Tappi J,* 50 (7): 363-368 (1967).
9. BERBEN, S. A., RADEMACHER, J. P., SELL, L. O., EASTY, D. B., "Estimation of Lignin in Wood Pulp by Diffuse Reflectance Fourier-transform Infrared Spectrometry", *Tappi J.,* 70(11): 129-133 (1987).
10. FAIX, O., PATT, R., "Method for Controlling the Digestion of Pulp by IR Spectroscopy", U.S. Pat. No. 4,743,339, May 10, 1988.
11. YUZAK, E., LOHRKE, C., "At-line Kappa Number Measurement by Near-Infrared Spectroscopy", Tappi Pulping Conference, 1993, p. 663-671.
12. BARRINGER, N., NORDER, S., "Method and Arrangement for Determining Fibre Properties by Near-Infrared-Spectroscopy", U.S. Pat. No. 5,536,942 (Jul. 16, 1996).
13. BADENLID, R., ANDERSON, S., "Method in Connection with the Production of Pulp, Paper or Paperboard", WO 01/79816 A1 (Oct. 25, 2001).
14. Birkett, M. D. and Gambino, M. J. T., "Estimation of pulp kappa number with near-infrared spectroscopy", Tappi J., 72(9): 193-197 (1989).
15. Millar, O. D., and Van Fleet, R. J., "Continuous In-line Kappa Measurement System", U.S. Pat. No. 5,953,111 (Sep. 14, 1999)
16. POKE, F. S., WRIGHT, J. K., and RAYMOND, C. A., "Predicting Extractives and Lignin Contents in *Eucalyptus Globulus* Using Near Infrared Reflectance Analysis", J. Wood Chem. Technol., 24(1), 55-67 (2004).
17. TRUNG, T. P., and LECLERC, D. F., "Method for Determining Lignin Content in Chemical Pulps Using Raman Spectrometry", U.S. Pat. No. 6,551,451 (Apr. 22, 2003).

The invention claimed is:

1. A method for determining a pulp property selected from lignin content or Kappa number of chemical pulp fibres comprising:
   a) exposing wet pulp fibres derived from at least partially digested wood chips to light covering a range in the visible region of 350 nm to 750 nm and a range in the near-infrared (NIR) region of 1100 to 2400 nm, and allowing the wet pulp fibres to reflect the light,
   b) collecting light reflected from said wet pulp fibres, wherein light covering the range of about 750 to 1100 nm is blocked out,
   c) establishing a spectrum of the reflected light,
   d) comparing said spectrum with a spectrum of chemical pulp fibres for which the pulp property is known, and
   e) evaluating the pulp property from the comparison in d).
2. A method according to claim 1 wherein said pulp property is lignin content.
3. A method according to claim 1 wherein said pulp property is Kappa number.
4. A method according to claim 1, wherein said light in the visible region is in a range of 400 nm to 750 nm.
5. A method according to claim 1, wherein said wet pulp fibres have a consistency of 8% to 30%.
6. A method according to claim 1, wherein said wet pulp fibres are mobile during steps a) and b).
7. A method according to claim 6, wherein said wet pulp fibres are found in a chamber during steps a) and b), and said chamber is rotated at a constant rate of revolution.
8. A method according to claim 1, wherein said collecting in step b) is for a predetermined period of time.
9. A method according to claim 4, wherein said collecting in step b) is for a predetermined period of time.
10. A method according to claim 8, wherein said period of time is less than 60 seconds.
11. A method according to claim 9, wherein said period of time is less than 10 seconds.
12. A method according to claim 1, wherein said wet pulp fibres in step a) are in a pulp manufacture line.
13. A method according to claim 12 wherein said step a) is carried out on wet pulp fibres at a plurality of locations in the manufacture line.
14. A method according to claim 13, wherein said plurality of locations is downstream of digestion of wood chips from which the pulp fibres are derived.
15. A method according to claim 3, wherein a Kappa number of 0.5 to 35 is evaluated in step e).

* * * * *